United States Patent [19]

Schweiss et al.

[11] 4,346,097
[45] Aug. 24, 1982

[54] METHOD FOR TREATING CONVULSIONS WITH PYRAZOLE-4-CARBOXAMIDE DERIVATIVES

[75] Inventors: Dietrich Schweiss; Ivan C. Nordin, both of Holland, Mich.

[73] Assignee: Warner-Lambert Company, Morris Plains, N.J.

[21] Appl. No.: 192,407

[22] Filed: Sep. 30, 1980

[51] Int. Cl.³ .......................................... A61K 31/415
[52] U.S. Cl. .............................. 424/273 P; 424/245; 424/248.54; 548/362; 548/104; 544/109
[58] Field of Search ............... 548/362, 104; 544/109; 424/245, 248.54, 273 P

[56] References Cited

U.S. PATENT DOCUMENTS 3,939,161  2/1976  Ratajczyk et al. ............... 544/118
4,134,987  1/1979  Huppatz ........................ 424/273 P

OTHER PUBLICATIONS

Shawali et al., J. Heterocyclic Chem. 1976, vol. 13, pp. 1137–1140.

Primary Examiner—Henry R. Jiles
Assistant Examiner—Natalia Harkaway
Attorney, Agent, or Firm—Stephen I. Miller

[57] ABSTRACT

New 5-amino-N-(substituted phenyl)-1,3-disubstituted-1H-pyrazole-4-carboxamides useful as anticonvulsant agents for treating warm-blooded animals are disclosed. Also disclosed are intermediates and methods for preparing the new compounds and methods for using the new compounds.

4 Claims, No Drawings

METHOD FOR TREATING CONVULSIONS WITH PYRAZOLE-4-CARBOXAMIDE DERIVATIVES

BACKGROUND OF THE INVENTION

Despite optimal use of the several antiepileptic drugs marketed in the United States, many patients with epilepsy fail to experience seizure control and others do so only at the expense of significant toxic side effects. In the early 1970's, no convincing evidence had been published that the primary antiepileptic drugs marketed in the United States at that time controlled the seizures of more than 50% or improved more than 75% of the patients with epilepsy. The availability and use of several additional drugs since that time has brought improved seizure control to many patients. Notwithstanding the beneficial effects of the current drugs, there is still a need for new antiepileptic drugs with more selective anticonvulsant effects and less toxicity. E. A. Swinyard, et al., Epilepsia, 19, 409 (1978).

SUMMARY OF THE INVENTION

The invention sought to be patented in a generic compound aspect is a compound having the structural formula I:

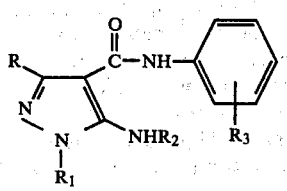

wherein R and $R_1$ may be the same or different and are alkyl of from 1 to 6 carbon atoms, phenyl, or benzyl; $R_2$ is hydrogen or alkyl of from 1 to 6 carbon atoms; $R_3$ is halo, alkyl of from 1 to 6 carbon atoms, amino, alkoxy of from 1 to 6 carbon atoms, nitro, trifluoromethyl, hydroxy, $CONR_4R_5$ wherein $R_4$ and $R_5$ may be the same or different and are hydrogen or alkyl of from 1 to 6 carbon atoms, or COOA wherein A is hydrogen, alkyl of from 1 to 6 carbon atoms, or a cation of a pharmaceutically acceptable metal or an amine; and the pharmaceutically acceptable salts thereof.

The invention sought to be patented in a subgeneric compound aspect is a compound having the structural formula:

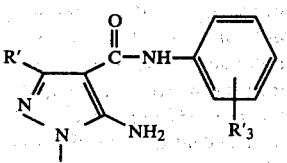

wherein R' and $R'_1$, may be the same or different and are alkyl of from 1 to 6 carbon atoms, $R'_3$ is halo or alkyl of from 1 to 6 carbon atoms; and the pharmaceutically acceptable salts thereof.

The preferred compounds of structural formula I are 5-amino-1,3-dimethyl-N-(2-methylphenyl)-1H-pyrazole-4-carboxamide; 5-amino-N-(3-chlorophenyl)-1,3-dimethyl-1H-pyrazole-4-carboxamide; 5-amino-N-(2-fluorophenyl)-1,3-dimethyl-1H-pyrazole-4-carboxamide; and the pharmaceutically acceptable salts thereof.

The invention sought to be patented in a second generic compound aspect is a compound having the structural formula VI:

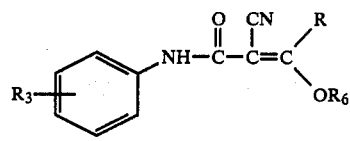

wherein R is alkyl of from 1 to 6 carbon atoms, phenyl, or benzyl; $R_3$ is halo, alkyl of from 1 to 6 carbon atoms, amino, alkoxy of from 1 to 6 carbon atoms, nitro, trifluoromethyl, hydroxy, $CONR_4R_5$ wherein $R_4$ and $R_5$ may be the same or different and are hydrogen or alkyl of from 1 to 6 carbon atoms, or COOA wherein A is hydrogen, alkyl of from 1 to 6 carbon atoms, or a cation of a pharmaceutically acceptable metal or amine; and $R_6$ is alkyl of from 1 to 6 carbon atoms. The preferred compounds of structural formula II are 2-cyano-3-ethoxy-N-(2-methylphenyl)crotonamide; 2-cyano-3-ethoxy-N-(3-chlorophenyl)crotonamide; and 2-cyano-3-ethoxy-N-(2-fluorophenyl)crotonamide.

The invention sought to be patented in its pharmaceutical composition aspect is a composition useful for treating convulsions in a warm blooded animal consisting essentially of a compound having the structural formula I:

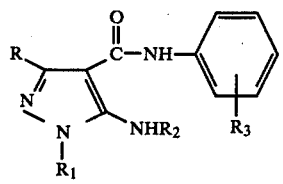

wherein R and $R_1$ may be the same or different and are alkyl of from 1 to 6 carbon atoms, phenyl, or benzyl; $R_2$ is hydrogen or alkyl of from 1 to 6 carbon atoms; $R_3$ is halo, alkyl of from 1 to 6 carbon atoms, amino, alkoxy of from 1 to 6 carbon atoms, nitro, trifluoromethyl, hydroxy, $CONR_4R_5$ wherein $R_4$ and $R_5$ may be the same or different and are hydrogen or alkyl of from 1 to 6 carbon atoms, or COOA wherein A is hydrogen, alkyl of from 1 to 6 carbon atoms, or a cation of a pharmaceutically acceptable metal or an amine; and the pharmaceutically acceptable salts thereof, in combination with a pharmaceutically acceptable carrier.

The pharmaceutical composition aspect of the invention also contemplates the use of mixtures of compounds each having the structural formula I in combination with a pharmaceutically acceptable carrier.

The pharmaceutical compositions contemplated by the invention are preferably provided in unit dose form.

The invention sought to be patented in its pharmaceutical method aspect is a method for treating convulsions in a warm blooded animal which comprises administering the above-defined pharmaceutical composition to a warm blooded animal in need thereof.

The invention sought to be patented in a first chemical method aspect is a method for preparing the compounds defined by structural formula I which comprises:

(a) reacting a pyrazole of structural formula II

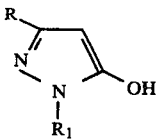

with a phenyl isocyanate of structural formula III

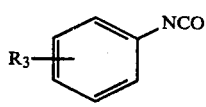

to produce a pyrazole of structural formula IV wherein R, $R_1$ and $R_3$ are defined above;

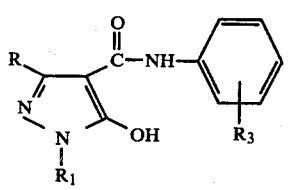

(b) converting the pyrazole of structural formula IV to the pyrazole of structural formula V wherein

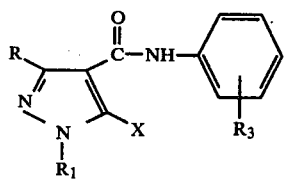

X is bromine or chlorine; and (c) reacting the pyrazole of structural formula V with an amine of the formula $R_2NH_2$, wherein $R_2$ is hydrogen or alkyl of from 1 to 6 carbon atoms.

The invention sought to be patented in a second chemical method aspect is a method for preparing the compounds defined by structural formula I wherein $R_2$ is hydrogen which comprises reacting a compound of the structural formula VI

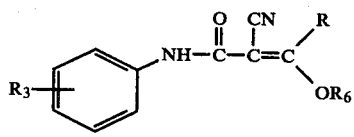

with a hydrazine of the formula $R_1NH-NH_2$, wherein R, $R_1$ $R_3$ and $R_6$ are defined above.

DESCRIPTION OF THE PREFERRED EMBODIMENTS

The starting compounds of structural formulae II and III are either commercially available or they are readily prepared by known methods or obvious variations thereof, see for example K. Auwers, J. Prakt. Chem. 110, 153 (1925). The reaction between II and III to produce IV may be carried out at temperatures of about 80° C. to about 150° C. in a non-reactive solvent until the reaction is substantially complete. The product is isolated and purified by standard procedures. A catalytic amount of a tertiary amine such as triethylamine or pyridine may be added, if desired, to improve the yield. The preferred solvents are the hydrocarbon solvents such as benzene, toluene and xylene; the most preferred solvent is xylene. In the preferred procedure, compounds II and III are mixed in xylene in the presence of a catalytic amount of triethylamine and refluxed for about 2 hours. The cooled reaction mixture is extracted with dilute aqueous base (e.g., 1 N sodium hydroxide). The aqueous phase is acidified with, for example, 1 N hydrochloric acid and the product is isolated by standard means, e.g., filtration.

Compound IV is converted to compound V by treatment with any of the standard halogenating agents in known manner. Examples of such halogenating agents are phosphorous tribromide, phosphorous trichloride, phosphorous oxybromide, phosphorous oxychloride, thionyl chloride, phenylphosphonic dichloride and the like. This conversion may be accomplished by contacting IV and the chosen halogenating agent at elevated temperature for about 6 hours. A non-reacting solvent such as benzene or xylene may be used or the reaction may be performed in the absence of a solvent. For reasons of convenience, the reactants may be contacted without applying any external heating for a brief period, e.g., 1 hour, prior to heating. Treatment of compound V with an amine of the formula $R_2NH_2$, wherein $R_2$ is hydrogen or alkyl of 1 to 6 carbon atoms e.g. ammonia or methylamine, in known manner will produce the desired products of structural formula I. Because this reaction generates a hydrogen halide, it is preferably carried out in the presence of an excess of the reacting amine, $R_2NH_2$, or in the presence of a non-interfering acid acceptor such as sodium bicarbonate or a tertiary amine e.g., triethylamine or pyridine. The final products may be isolated and purified by standard procedures.

The final products of structural formula I wherein $R_2$ is hydrogen may also be prepared by reacting a properly substituted crotonamide of structural formula VI with a monoalkyl-substituted hydrazine. This reaction may be accomplished by mixing the two reactants in a nonreactive solvent, such as ethanol, at elevated temperature until the reaction is substantially complete. For example, at 80° C. for about 1 to about 10 hours. The isolation and purification of the final product is within the skill of the art.

The crotonamides of structural formula VI may be efficiently prepared by mixing a 2-cyanoacetanilide and an orthoester at elevated temperature in a reaction-inert solvent in the presence of a dehydrating agent. A hydrocarbon solvent such as toluene, or xylene and a dehydrating agent such as acetic anhydride may be utilized. Other useful solvents and dehydrating agents will be familiar to those skilled in the art. The reaction is conveniently carried out at the reflux temperature of the solvent until the reaction is substantially complete. For example, 125° C. for a period of about 4 to about 24 hours. Any orthoester may be utilized, and those skilled in the art will recognize that the alkyl portion of the orthoester becomes the 3-position substituent in the final product I. Thus, if an orthoester of acetic acid, for example triethyl orthoacetate, is utilized the final product will contain a methyl substituent in the 3-position.

The 2-cyanoacetanalides may be prepared from cyanoacetic acid and a substituted aniline by methods familiar to those skilled in the art. For example, the desired aniline may be treated in a known manner with cyanoacetylchloride or a cyanoacetic acid ester.

The compounds of structural formula I are basic in nature and form pharmaceutically acceptable salts with both organic and inorganic acids. Examples of such acids are acetic, hydrochloric, phosphoric, nitric, sulfuric, fumaric, citric, maleic, malic and the like. The salts are prepared by contacting the free base form of the pyrazole with an equivalent amount of the desired acid in the conventional manner. The free base forms may be regenerated by treating the salt form with a base. For example, dilute aqueous basic solutions may be utilized. Dilute aqueous sodium hydroxide, sodium carbonate or ammonia are suitable for this purpose. The free base forms differ from their respective salt forms somewhat in certain physical properties such as solubility in polar solvents, but the salts are otherwise equivalent to their respective free base forms for purposes of the invention.

The compounds of the invention of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

The alkyl groups, and alkoxy groups contemplated by the invention comprise both straight and branched carbon chains of from 1 to about 6 carbon atoms. Representative of such groups are methyl, ethyl, isopropyl, pentyl, 3-methylpentyl, methoxy, ethoxy, propoxy, 1-ethylbutoxy, pentoxy and the like. The term halo is intended to include fluorine, chlorine, bromine and iodine. Pharmaceutically acceptable metal cations are intended to include the cations of the alkali and alkaline earth metals, e.g. sodium, potassium, magnesium, calcium and the like; also intended is aluminum and the cations of other pharmaceutically compatible metals. Pharmaceutically acceptable amine cations are the positively charged ammonium, substituted-ammonium and cyclic ammonium ions derived from organic nitrogenous bases strong enough to form such cations. Illustrative of such cations are ammonium, mono, di and trialkylammonium, cyclohexylammonium, benzyammonium, piperidinium, morpholinium, pyrrolidinium, pyridinium, and the like.

The compounds of structural formula I are new chemical substances of value as pharmacological agents for the treatment of convulsions in warm-blooded animals. The term convulsions is intended to mean the characteristic body movements which are associated with the group of chronic central nervous system disorders termed, epilepsies. The anticonvulsant activity of representative compounds of formula I was established by the following standard test procedures:

1. Rotorod Test, $TD_{50}$.
2. Maximal Electroshock Seizure Test, MES.
3. Subcutaneous Pentylenetetrazole Seizure Threshold Test, scMet.

These procedures are described in E. A. Swinyard, et al., Epilepsia, 19, 409 (1978), which is incorporated herein by reference. The $TD_{50}$ is defined as the median minimal neurotoxic dose.

The following table gives the profile of anticonvulsant activity for two substituted pyrazoles of the invention, and four standard anticonvulsant compounds known to those skilled in the art.

| COMPOUND | $TD_{50}$ (mg/kg) | $ED_{50}$ (mg/kg) MES | $ED_{50}$ (mg/kg) scMet | $PI^a$ MES | $PI^a$ scMet |
|---|---|---|---|---|---|
| 5-AMINO-1,3-DIMETHYL-N-(2-METHYL-PHENYL)-1H-PYRAZOLE-4-CARBOXAMIDE | 103.94 | 25.69 | 53.67 | 4.05 | 1.94 |
| 5-AMINO-1,3-DIMETHYL-N-(3-CHLORO-PHENYL)-1H-PYRAZOLE-4-CARBOXAMIDE | 234.12 | 47.26 | 99.58 | 4.95 | 2.35 |
| PHENYTOIN | 65.46 | 9.50 | POTENTIATES | 6.89 | — |
| PHENOBARBITAL | 69.01 | 21.78 | 13.1 | 3.17 | 5.24 |
| CARBAMAZEPINE | 71.56 | 8.81 | POTENTIATES | 8.12 | — |
| MEPHENYTOIN | 153.82 | 60.50 | 30.45 | 2.54 | 5.05 |

$^a$Protective Index, Ratio of $TD_{50}$ vs $ED_{50}$ MES or scMet

The compounds of structural formula I can be prepared and administered in a wide variety of oral and parenteral dosage forms.

For preparing pharmaceutical compositions from the compounds described by this invention, inert, pharmaceutically-acceptable carriers can be either solid or liquid. Solid form preparations include powders, tablets, dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound of formula I. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

Liquid form preparations include solutions, suspensions and emulsions. As an example may be mentioned water or water-propylene glycol solutions for parenteral injection. Liquid preparations can also be formulated in solution in aqueous polethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e. natural or synthetic gums, resins, methyl cellulose, sodium carboxymethyl cellulose and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from 1 mg to 100 mg according to the particular application and the potency of the active ingredient.

In therapeutic use as agents for treating convulsions, the compounds utilized in the pharmaceutical method of this invention are administered at the initial dosage of about 0.1 mg to about 21 mg per kilogram daily. A daily dose range of about 0.35 mg to about 12 mg per kilogram is preferred. The dosages, however, may be varied depending upon the requirements of the patient, the severity of the condition being treated and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following non-limiting examples illustrate the inventor's preferred methods for preparing the compounds of the invention.

EXAMPLES

EXAMPLE 1

5-Amino-1,3-dimethyl-N-(2-methylphenyl)-1H-pyrazole-4-carboxamide 24.4 g (0.1 mol) of 2-cyano-3-ethoxy-N-(2-methylphenyl)crotonamide in 150 ml absolute ethanol is stirred at room temperature. 6 ml (0.11 mol) of monomethylhydrazine in 10 ml absolute ethanol is added dropwise. The resulting solution is heated to reflux for 2 hrs., then stirred at room temperature overnight.

The reaction mixture is cooled to $-5°$ C., the solid is collected, and washed with cold ethanol. The product is dried to give 18.5 g of 5-amino-1,3-dimethyl-N-(2-methylphenyl)-1H-pyrazole-4-carboxamide a white solid which is recrystallized from water, mp. of 113°–115° C.

Analysis calculated: 63.92% C, 6.61% H, 22.93% N. Found: 63.84% C, 6.86% H, 22.88% N.

The hydrochloride salt of the product (from acetone) has a mp. of 240°–242° C. with decomposition.

EXAMPLE 2

5-Amino-N-(3-chlorophenyl)-1,3-dimethyl-1H-pyrazole-4-carboxamide 26.5 g (0.1 mol) of N-(3-chlorophenyl)-2-cyano-3-ethoxy-crotonamide in 150 ml absolute ethanol is stirred at room temperature. 6 ml (0.11 mol) of monomethylhydrazine in 10 ml absolute ethanol is added dropwise. The resulting solution is heated to reflux for 2 hrs. and is then stirred at room temperature overnight.

The ethanol is stripped at reduced pressure. The residue is dissolved in 1000 ml water and 100 ml ethanol with heating. The hot solution is treated with charcoal and is then filtered. The filtrate is cooled, seeded and refrigerated overnight. The crystals are collected and washed with water. The product is dried to give 19.2 g of 5-amino-N-(3-chlorophenyl)-1,3-dimethyl-1H-pyrazole-4-carboxamide as an off white solid. The mp. is 87°–92° C. after recrystallization from water containing 10% ethanol.

Analysis calculated: 54.48% C, 4.95% H, 21.15% N. Found: 54.29% C, 4.98% H, 21.27% N.

EXAMPLE 3

5-Amino-N-(2-fluorophenyl)-1,3-dimethyl-1H-pyrazole-4-carboxamide, monohydrate 37 g (0.15 mol) of 2-cyano-3-ethoxy-N-(2-fluorophenyl)crotonamide is stirred in 150 ml absolute ethanol at reflux temperature. 10 ml (0.16 mol) of monomethylhydrazine in 10 ml absolute ethanol is added dropwise. The resulting solution is refluxed for 5 hrs., then stirred at room temperature overnight. The ethanol is stripped at reduced pressure. The residue is dissolved in toluene. The solution is treated with 250 ml of a 2 N solution of hydrochloric acid. The precipitated hydrochloric salt is collected and is combined with the aqueous phase of the filtrate. The mixture is made basic with concentrated ammonium hydroxide. The slurry is cooled and the solid is collected and dried to give 29.5 g of 5-amino-N-(2-fluorophenyl)-1,3-dimethyl-1H-pyrazole-4-carboxamide, monohydrate as a white solid. The product is the monohydrate and melts at 101°–103° C. after recrystallization from a mixture of ethylacetate and petroleum ether.

Analysis calculated: 54.13% C, 5.67% H, 21.04% N, 6.76% $H_2O$. Found: 54.33% C, 5.62% H, 20.78% N, 6.39% $H_2O$.

EXAMPLE 4

2-Cyano-3-ethoxy-N-(2-methylphenyl)crotonamide 122 g (0.7 mol) of 2-cyano-o-acetotoluidide (CA 22:2353/6 and CA 60:2840C) is slurried in a mixture of 250 ml toluene and 139 ml (0.76 mol) triethyl orthoacetate and heated to reflux.

142 ml (1.5 mol) of acetic anhydride is added dropwise over a period of 2 hrs.

The resulting solution is refluxed for an additional 3 hrs. then stirred at room temperature overnight.

The solvent is stripped at reduced pressure. The residue is suspended in 400 ml ethanol, cooled to 0°–5° C. and 50 ml of morpholine is added. The solid is collected, washed with ethanol. The product is dried to yield 66 g of off white needles of mp. 179°–180° C. Recrystallization from absolute ethanol gives 2-cyano-3-ethoxy-N-(2-methylphenyl)crotonamide as white needles of mp. 179°–181° C.

Analysis calculated: 68.86% C, 6.61% H, 11.45% N. Found: 69.15% C, 6.77% H, 11.31% N.

EXAMPLE 5

2-Cyano-3-ethoxy-N-(3-chlorophenyl)crotonamide 97.3 g (0.5 mol) of 3′-chloro-2-cyano-acetanilide (CA 60:2840C) is slurried in a mixture of 200 ml toluene, 99 ml (0.54 mol) triethyl orthoacetate and 103.5 ml (1.1 mol) acetic anhydride. The reaction mixture is heated to reflux for 4 hrs.

The resulting solution is stirred at room temperature overnight.

The solvent is stripped at reduced pressure. The residue is triturated with 350 ml cold absolute ethanol. The solid is collected and washed with cold ethanol. 55 g of 2-cyano-3-ethoxy-N-(3-chlorophenyl)crotonamide as a white solid is obtained, which after recrystallization from absolute ethanol has a mp. of 166°–168° C.

Analysis calculated: 58.99% C, 4.95% H, 10.58% N. Found: 59.18% C, 5.15% H, 10.70% N.

EXAMPLE 6

2-Cyano-3-ethoxy-N-(2-fluorophenyl)crotonamide 90 g (0.5 mol) of 2-cyano-2'-fluoroacetanilide (mp. 113°–115° C., CA 60:2840C) is slurried in a mixture of 250 ml toluene and 100 ml (0.54 mol) triethyl orthoacetate. The mixture is heated to reflux and 103.5 ml (1.1 mol) acetic anhydride is added dropwise over the course of 2 hrs. The refluxing is continued for 24 hrs.

The resulting solution is stripped at reduced pressure. The solid residue is heated with 300 ml absolute ethanol, cooled and refrigerated. The solid is collected and washed with ethanol. The product is dried to give 80 g of 2-cyano-3-ethoxy-N-(2-fluorophenyl)crotonamide as an off white solid. The mp is 158°–160° C. after recrystallization from absolute ethanol.

Analysis calculated: 62.89% C, 5.27% H, 11.28% N. Found: 63.07% C, 5.35% H, 11.08% N.

PREPARATIVE EXAMPLES

Preparative Example 1

5-Hydroxy-1,3-dimethyl-N-(2-methylphenyl)-1H-pyrazole-4-carboxamide

A mixture of 22.4 g (0.2 mol) 5-hydroxy-1,3-dimethyl-1H-pyrazole [K. Auwers, J.Prakt.Chem., 110, 153 (1925)], 26.6 g (0.2 mol) o-tolylisocyanate in 150 ml xylene containing 1 ml triethylamine is heated to reflux for 1.5 hours.

The reaction mixture is cooled and extracted with 200 ml of a 1 N aqueous sodium hydroxide solution. The aqueous phase is separated, filtered and then acidified with 120 ml of a 1 N solution of hydrochloric acid.

The precipitate is collected and washed with water. The crude product is recrystallized from a mixture of 120 ml ethanol and 200 ml water, giving 29.5 g of a nearly white solid of mp. 208°–210° C. (with decomposition).

Analysis calculated: 63.67% C, 6.16% H, 17.12% N. Found: 63.85% C, 6.33% H, 17.32% N.

Preparative Example 2

5-Chloro-1,3-dimethyl-N-(2-methylphenyl)-1H-pyrazole-4-carboxamide

A mixture of 11.6 g (50 mmol) 5-hydroxy-1,3-dimethyl-N-(2-methylphenyl)-1H-pyrazole-4-carboxamide and 100 ml phosphorous oxychloride is stirred at room temperature for 0.5 hours and then at reflux temperature for 2 hours.

The solution is stripped at reduced pressure. The residue is dissolved in 200 ml dichloromethane and treated with 200 g crushed ice. The dichloromethane layer is separated, washed with 100 ml cold water and then 100 ml of a 0.5 N solution of sodium hydroxide. The dichloromethane extract is then dried over magnesium sulfate and filtered. The filtrate is stripped at reduced pressure, leaving 6.5 g of a pale yellow solid. Recrystallization from toluene gives white needles of mp. 149°–151° C.

Analysis calculated: 57.70% C, 4.85% H, 16.83% N. Found: 57.79% C, 5.00% H, 17.04% N.

I claim:

1. A method for treating convulsions in a warm blooded animal which comprises administering to said warm blooded animal an anticonvulsive effective amount of at least one compound having the structural formula:

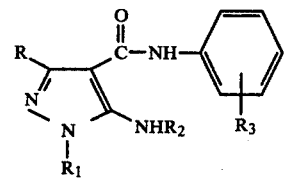

wherein R and $R_1$ may be the same or different and are alkyl of from 1 to 6 carbon atoms, phenyl, or benzyl; $R_2$ is hydrogen or alkyl of from 1 to 6 carbon atoms, $R_3$ is halo, alkyl of from 1 to 6 carbon atoms, amino, alkoxy of from 1 to 6 carbon atoms, nitro, trifluoromethyl, hydroxy, $CONR_4R_5$ wherein $R_4$ and $R_5$ may be the same or different and are hydrogen or alkyl of from 1 to 6 carbon atoms, or COOA wherein A is hydrogen, alkyl of from 1 to 6 carbon atoms, or a cation of a pharmaceutically acceptable metal or an amine; and the pharmaceutically acceptable salts thereof.

2. The method defined in claim 1 wherein the compound is 5-amino-N-(3-chlorophenyl)-1,3-dimethyl-1H-pyrazole-4-carboxamide.

3. The method defined in claim 1 wherein the compound is 5-amino-N-(2-methylphenyl)-1,3-dimethyl-1H-pyrazole-4-carboxamide.

4. The method defined in claim 1 wherein the compound is 5-amino-N-(2-fluorophenyl)-1,3-dimethyl-1H-pyrazole-4-carboxamide.

* * * * *